US012156702B2

(12) United States Patent
Siemionow et al.

(10) Patent No.: US 12,156,702 B2
(45) Date of Patent: Dec. 3, 2024

(54) METHOD AND APPARATUS FOR REGISTERING A NEUROSURGICAL PATIENT AND DETERMINING BRAIN SHIFT DURING SURGERY USING MACHINE LEARNING AND STEREOOPTICAL THREE-DIMENSIONAL DEPTH CAMERA WITH A SURFACE-MAPPING SYSTEM

(71) Applicant: Inteneural Networks Inc., Chicago, IL (US)

(72) Inventors: Kris Siemionow, Chicago, IL (US); Marek Kraft, Poznan (PL); Michal Mikolajczak, Poznan (PL); Dominik Pieczynski, Tulce (PL); Mikolaj Pawlak, Poznan (PL); Michal Klimont, Poznan (PL); Paul Lewicki, Tulsa, OK (US)

(73) Assignee: INTENEURAL NETWORKS INC., Chicago, IL (US)

( * ) Notice: Subject to any disclaimer, the term of this patent is extended or adjusted under 35 U.S.C. 154(b) by 253 days.

(21) Appl. No.: 17/836,091

(22) Filed: Jun. 9, 2022

(65) Prior Publication Data

US 2022/0401148 A1 Dec. 22, 2022

Related U.S. Application Data

(60) Provisional application No. 63/209,294, filed on Jun. 10, 2021.

(30) Foreign Application Priority Data

Sep. 17, 2021 (EP) ..................................... 21197358

(51) Int. Cl.
*A61B 34/10* (2016.01)
*A61B 90/00* (2016.01)
(Continued)

(52) U.S. Cl.
CPC ................ *A61B 34/10* (2016.02); *G06T 7/37* (2017.01); *G06T 17/00* (2013.01);
(Continued)

(58) Field of Classification Search
CPC ..... G06T 7/30–38; G06T 7/0012–0016; G06T 17/00–30; A61B 34/10–25
See application file for complete search history.

(56) References Cited

U.S. PATENT DOCUMENTS

2007/0021669 A1 1/2007 Miga et al.
2011/0257514 A1\* 10/2011 Bucki ...................... G06T 7/38
600/407
(Continued)

*Primary Examiner* — Carolyn A Pehlke
(74) *Attorney, Agent, or Firm* — Rivka Friedman

(57) ABSTRACT

A method for generating an intraoperative 3D brain model while a patient is operated. Before an opening in a patient's skull is made, the method includes: providing a preoperative 3D brain model of a patient's brain and converting it to a preoperative 3D brain point cloud; providing a preoperative 3D face model of a patient's face and converting it to a preoperative 3D face point cloud. After the opening in the patient's skull is made, the method includes: matching the intraoperative 3D face point cloud with the preoperative 3D face point cloud to find a face point transformation; transforming the intraoperative 3D brain point cloud based on said face point cloud transformation; comparing the intraoperative 3D brain point cloud with the preoperative 3D brain point cloud to determine a brain shift; and converting the preoperative 3D brain model to generate an intraoperative 3D brain model based on said brain shift.

10 Claims, 4 Drawing Sheets

(51) Int. Cl.
  *G06T 7/37* (2017.01)
  *G06T 17/00* (2006.01)
(52) U.S. Cl.
  CPC ... *A61B 2034/105* (2016.02); *A61B 2090/364* (2016.02); *A61B 2090/371* (2016.02); *G06T 2200/08* (2013.01); *G06T 2207/10012* (2013.01); *G06T 2207/10028* (2013.01); *G06T 2207/10081* (2013.01); *G06T 2207/10088* (2013.01); *G06T 2207/30016* (2013.01); *G06T 2207/30201* (2013.01)

(56) References Cited

U.S. PATENT DOCUMENTS

| | | | |
|---|---|---|---|
| 2015/0335390 A1* | 11/2015 | Gill | A61B 6/032 600/424 |
| 2020/0051274 A1 | 2/2020 | Siemionow et al. | |
| 2020/0138518 A1 | 5/2020 | Lang | |
| 2021/0082565 A1 | 3/2021 | Kraft et al. | |

* cited by examiner

METHOD AND APPARATUS FOR REGISTERING A NEUROSURGICAL PATIENT AND DETERMINING BRAIN SHIFT DURING SURGERY USING MACHINE LEARNING AND STEREOOPTICAL THREE-DIMENSIONAL DEPTH CAMERA WITH A SURFACE-MAPPING SYSTEM

TECHNICAL FIELD

The present disclosure generally relates to registering a neurosurgical patient and machine learning systems and methods suitable for determining brain shift during surgery using stereo optical three-dimensional depth camera with a surface-mapping system.

BACKGROUND

Neurosurgical procedures such as deep brain stimulation (DBS) or lesion resection are increasingly used to treat a wide variety of neurological disorders. For example, there have been approximately 40,000 patients world-wide that have undergone DBS surgery. Consequently, there is a large population of patients who will benefit from advances in neurosurgical treatment options.

During the surgical procedure, at least one burr hole is cut through the patient's cranium. When the dura is punctured to access brain tissue, during the DBS or tumor resection procedure the brain may shift due to a change of pressure. Brain shift may include the movement and deformation of the brain during an operation. Brain shift is a prevalent source of significant error in the implantation of stimulation leads or co-registration of preoperative Magnetic Resonance Imaging (MRI) and Computed Tomography (CT) scan images.

Similarly, when an opening is created in the skull for the purpose of a brain surgery procedure, the brain may shift. Consequently, preoperative brain images that were collected e.g. by MRI, are no longer representative and do not reflect the actual shape and position of the brain and cannot be used directly to aid in the operative procedure.

The risk associated with the procedure is the combined outcome of the probability to miss the target of the procedure, injury of the artery in the course of the intervention path, injury of the vein along the intervention path and injury of the neural region or pathway along the way. Misallocation of the target comes from the shift caused by brain moving away from its original position because of air entering the intracranial volume following drilling a hole in the skull.

SUMMARY OF THE INVENTION

To correct for the process of brain shift, the present invention proposes use of a deformation model that takes into account preoperative imaging data from CT, MRI, MRA and imaging information from the intraoperative optical imaging system as described herein. The risk of the injuring the arteries and veins is minimized by identification of flow and venous deoxygenated blood using Time-of-flight magnetic resonance angiography for arteries, Phase Contrast magnetic resonance angiography for both veins and arteries and susceptibility weighted imaging for veins. Extracting the position of veins and arteries from the individual sequences and combining them into vascular map enables the system to identify the potential conflicts of the intervention path with the vessels that might result in bleeding. To avoid the conflict and reach the target, a system is proposed for optimizing planning using nonlinear approach. It will be applicable in case where linear advancing towards the target might result in vascular damage and risking missing the target of the intervention.

Brain misalignment in comparison to preoperative image-based model can be computed and used to deform the previously mentioned vascular map in order to improve the reliability and safety of the procedure.

Therefore, there is a need to determine the brain shift during surgery such as to facilitate use of preoperative registered brain models. Brain shift is a prevalent source of significant error in the implantation of stimulation leads. Brain shift may include the movement and deformation of the brain during an operation. For example, when the dura is punctured to access brain tissue during the deep brain stimulation lead implantation procedure. Sub-cranial contents may shift significantly due to cerebrospinal fluid (CSF) leaking out of the burr hole, which causes a change in intracranial pressure. Surgeons rely on pre-operative CT and MRI scans to precisely localize the targets for electrode placement. These targets must be localized and the electrodes delivered with millimeter-quality accuracy. During the surgical procedure, fixed fiducials on the surface of the skull are used as reference points for the insertion of electrodes. These fiducials cannot take into account the shifting of the intracranial contents, and by the time the actual electrodes are implanted, the CT/MRI guiding the physicians is inaccurate. Over the course of a surgical procedure, comprehensive studies have often recorded average brain displacements approaching or exceeding ten millimeters, which is an unacceptable margin of error. The result forces the surgeons doctors to use approximations in order to localize regions deep within the brain.

Brain shift is generally caused by settling of the brain, often facilitated by a leakage of CSF and the resulting decrease of intracranial pressure and buoyancy. Brain shift is not always uniform deep within the tissue, adding the complication of deformation. The primary force driving brain shift is gravity, though deformation could potentially be caused by osmotic drugs that change intracranial water concentration. A study of pre-operation MRIs has shown that brain shift from changes in patient position is insignificant (less than 1 mm). To address these issues, there are several protocols now being developed to compensate for the discrepancy between the MRI and the shifted brain. The most effective of these involve intra-operative MRIs, ultrasounds, or optical scanners designed to update the MRI over the course of the surgery. The present disclosure generally relates using a stereo optical three-dimensional depth camera with a surface-mapping system that allows for identification and characterization of the brain shift in real time. A neural network is used for interpretation of the newly generated three-dimensional image. The neural network is used to update the preoperative MRI to account for changes observed intraoperatively.

The invention described herein is particularly useful for determining brain shift during surgery such as to facilitate determining actual position of specific structures of the brain as known from the preoperative model.

The invention relates to a method for generating an intraoperative 3D brain model while a patient is operated. Before an opening in a patient's skull is made, the method includes providing a preoperative 3D brain model of patient's brain; converting the preoperative 3D brain model to a preoperative 3D brain point cloud; providing a preoperative 3D face model of a patient's face; and converting the preoperative 3D face model to a preoperative 3D face point cloud. After the opening in the patient's skull is made, the method includes receiving an intraoperative 3D face point cloud and an intraoperative 3D brain point cloud; matching the intraoperative 3D face point cloud with the preoperative 3D face point cloud to find a face point transformation; transforming the intraoperative 3D brain point cloud based on said face point cloud transformation; comparing the intraoperative 3D brain point cloud with the preoperative 3D brain point cloud to determine a brain shift; and converting the preoperative 3D brain model to generate an intraoperative 3D brain model based on said brain shift.

The method may further comprise generating the preoperative 3D brain model based on preoperative magnetic resonance imaging scan of patient's brain.

The method may further comprise generating the preoperative 3D face model based on preoperative computed tomography scan of patient's face.

The method may further comprise receiving the intraoperative 3D face point cloud and the intraoperative 3D brain point cloud from a stereoscopic depth camera, a camera using projected light or a time of flight 3D sensor.

The method may further comprise determining the brain shift for the intraoperative 3D brain point cloud received as first after the opening in the patient's skull is made by using rigid transformation algorithms and for subsequent intraoperative 3D brain point clouds received, by using elastic registration algorithms.

The invention also relates to a computer-implemented system, comprising: at least one nontransitory processor-readable storage medium that stores at least one of processor-executable instructions or data; and at least one processor communicably coupled to at least one nontransitory processor-readable storage medium, wherein at least one processor is configured to perform the steps of the method as described above.

These and other features, aspects and advantages of the invention will become better understood with reference to the following drawings, descriptions and claims.

BRIEF DESCRIPTION OF DRAWINGS

Various embodiments are herein described, by way of example only, with reference to the accompanying drawings, wherein.

DETAILED DESCRIPTION

The following detailed description is of the best currently contemplated modes of carrying out the invention. The description is not to be taken in a limiting sense, but is made merely for the purpose of illustrating the general principles of the invention.

Figure 2:
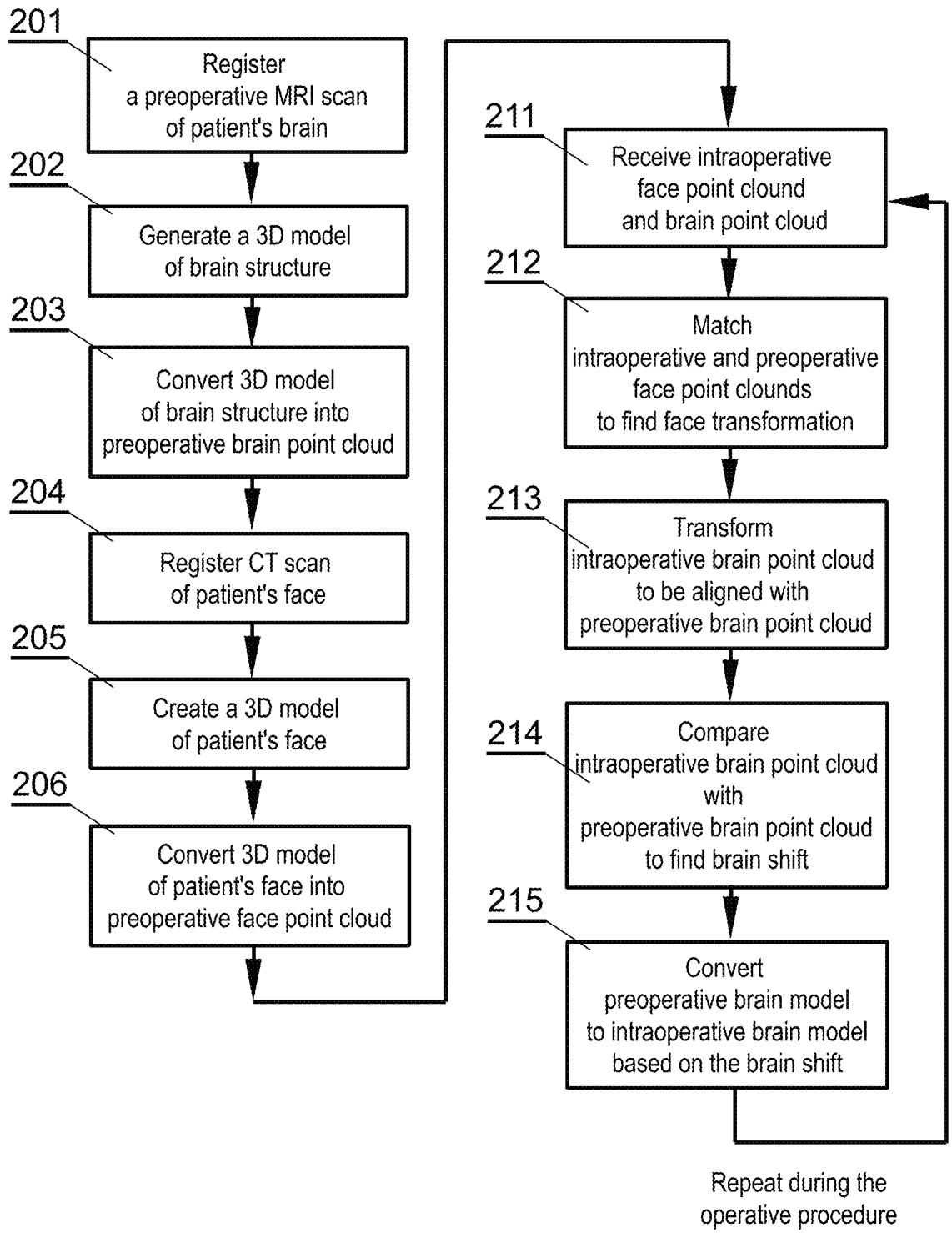
FIG. 2 shows a procedure for registering a patient and determining brain shift during surgery.

FIG. 2 shows a procedure for registering a patient and determining brain shift during surgery.

Figure 1A:
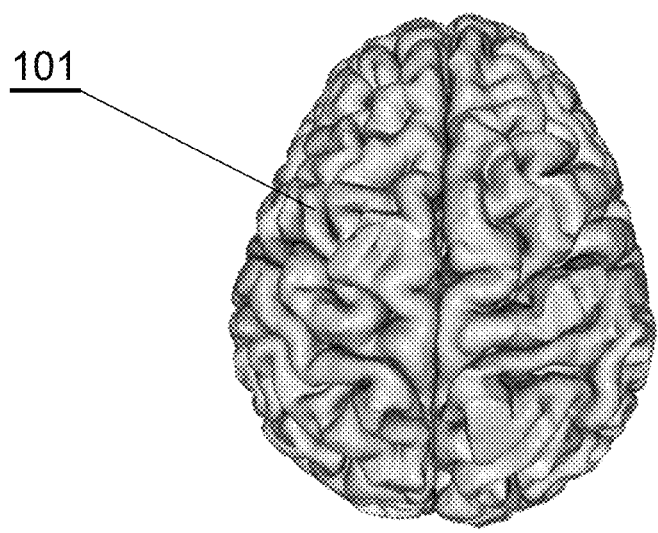
FIG. 1A shows an example of a preoperative 3D brain model.
Figure 1B:
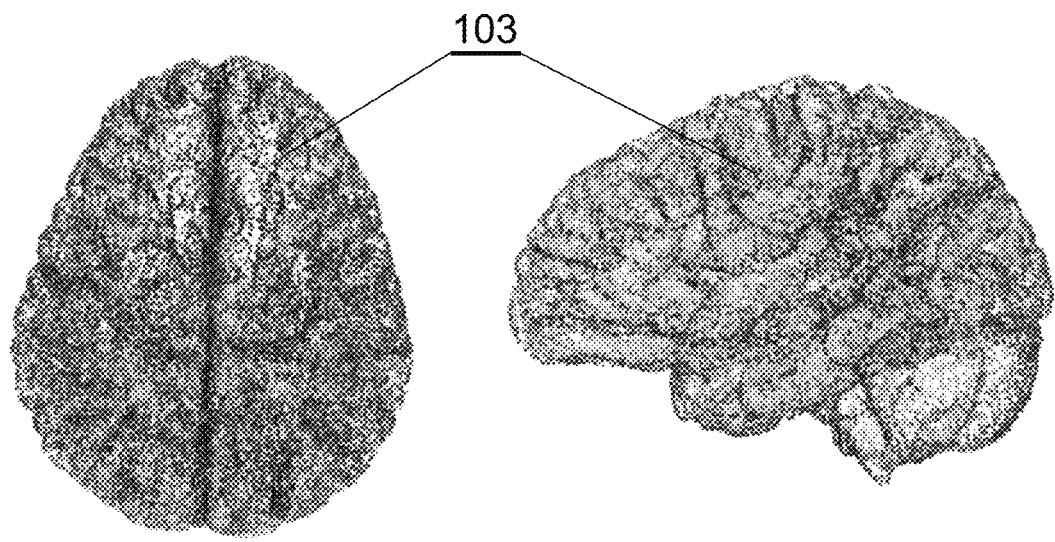
FIG. 1B shows an example of the preoperative 3D brain model converted to preoperative 3D brain point cloud.

First, in step 201 a preoperative MRI scan of a patient's brain is received. The MRI scan (after necessary pre-processing such as combining 2D slices into a 3D volume and performing skull stripping to obtain only the brain image data) is input in step 202 to a segmentation artificial intelligence module that generates a 3D model 102 of the brain structure with annotated segments, as shown in FIG. 1A. Next, in step 203 the preoperative 3D brain model is converted into a preoperative 3D brain point cloud 103 as shown in FIG. 1B (shown in a top view on the left and a side view on the right).

Figure 1C:
FIG. 1C shows an example of the preoperative 3D face point cloud.

In addition, in step 204 a CT scan of a patient's face is registered. The CT scan is input in step 205 to a mask creating module that creates a 3D mask of the face appearance. This can be done by an artificial intelligence module (such as a trained convolutional neural network (CNN)) or a scatter plot can be created to emulate a map. In step 206, the 3D mask that defines a preoperative 3D face model is converted into a preoperative 3D face point cloud 106 as shown in FIG. 1C.

Figure 1D:
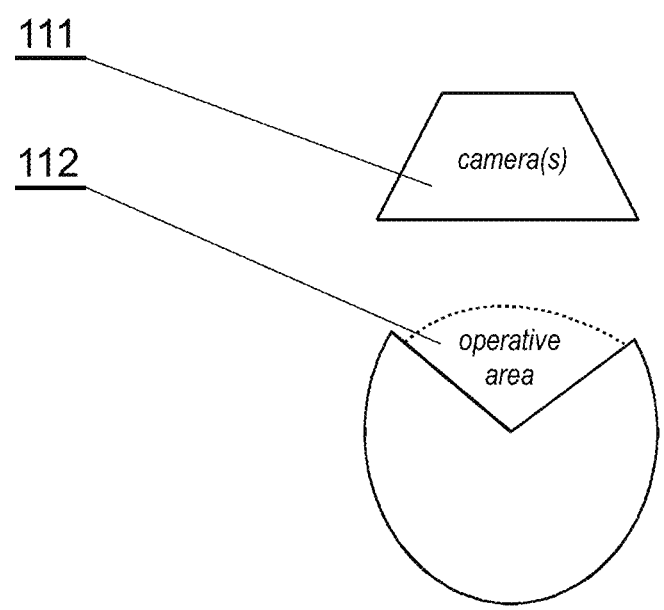
FIG. 1D shows schematically a setup of intraoperative depth camera(s)

Next, while the patient is subject to an operating procedure, an intraoperative 3D face point cloud and an intraoperative 3D brain point cloud that includes the operative area 112 are received from at least one camera 111 in step 211. FIG. 1D shows schematically an example setup of the camera(s) 111. Preferably, the camera(s) 111 are stereoscopic camera(s). For example, a single stationary depth camera can be used. Alternatively, a plurality of depth cameras can be used, stationary or movable. Other possible camera(s) include cameras using projected light or time of flight 3D sensors. Furthermore, camera(s) using projected light can be used. In case a movable camera is used, an algorithm can be used to register the currently captured image with the preoperative 3D brain point cloud 103.

In step 212 the intraoperative 3D face point cloud is matched to the preoperative 3D face point cloud in order to align these point clouds, i.e. to find a face point cloud transformation that defines a spatial transformation between the two point clouds (for example, defining the rotation and shift of one cloud with respect to the other, as well as its scaling if necessary).

In step 213 the intraoperative 3D brain point cloud is spatially transformed based on said face point cloud transformation, so that it is aligned with the preoperative 3D brain point cloud.

Next, in step 214 the brain shift can be determined by comparing the preoperative 3D brain point cloud with the intraoperative 3D brain point cloud (which changes due to pressure taking effect). This can be done for example by first using a fast global algorithm (as described at vladlen.info/publications/fast-global-registration/) with robust outlier rejection using the random sample consensus (RANSAC) algorithm (as described at en.wikipedia.org/wiki/Random_sample_consensus). After the initial alignment is achieved, the results can be further refined using the iterative closest point (ICP) algorithm (as described at https://en.wikipedia.org/wiki/Iterative_closest_point). This can be followed by the coherent point drift (CPD) algorithm, to ensure nonrigidity is handled properly (as described at arxiv.org/pdf/0905.2635.pdf). Therefore, in other words, since brain is not a rigid body, at the beginning a rigid transformation is used and next elastic registration is used, as the brain may deform more freely.

Finally, in step 215 the preoperative brain model is converted into an intraoperative 3D brain model by applying thereon the brain shift determined based on the comparison of point clouds. Such intraoperative 3D brain model can be then used for real time assistance in the surgical procedure to determine location of specific parts of brain anatomy during the operation.

Steps 213-215 can be operated in a loop, such as to compensate for potential further brain shifts during the operation. 3D displacements of the surface features captured by the depth map are recorded by the depth camera in real time and the intraoperative 3D brain model is updated continuously to accommodate the brain shift. Therefore, intraoperative locations of particular parts of the organ or a lesion can be monitored.

In particular, the deformation can be adapted or constrained to model locations and dimensions of surgical cavities using deformable, non-rigid point cloud registration method and/or locations of surgical instruments in the organ.

Figure 3:
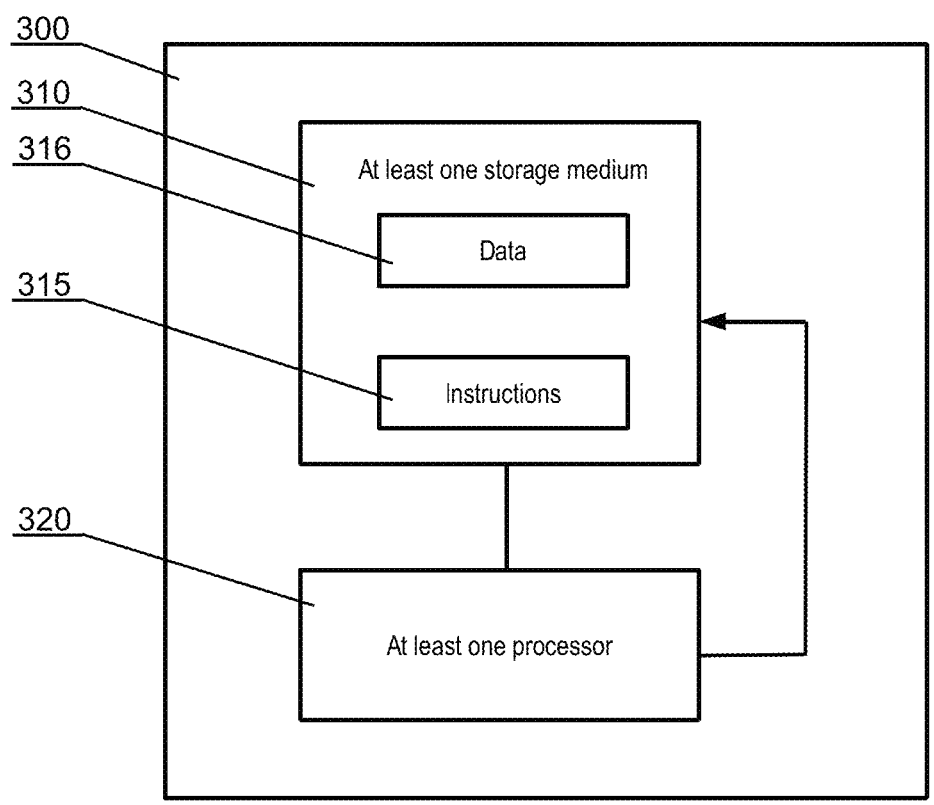
FIG. 3 shows the structure of a computer system for implementing the method of FIG. 2.

The functionality described herein can be implemented in a computer-implemented system 300, such as shown in FIG. 3. The system may include at least one non-transitory processor-readable storage medium that stores at least one of processor-executable instructions or data and at least one processor communicably coupled to at least one non-transitory processor-readable storage medium. At least one processor is configured to perform the steps of the methods presented herein.

The computer-implemented system 300, for example a machine-learning system, may include at least one non-transitory processor-readable storage medium 310 that stores at least one of processor-executable instructions 315 or data 316; and at least one processor 320 communicably coupled to the at least one non-transitory processor-readable storage medium 310. At least one processor 320 may be configured to (by executing the instructions 315) to perform the steps of the method of FIG. 2.

While the invention has been described with respect to a limited number of embodiments, it will be appreciated that many variations, modifications and other applications of the invention may be made. Therefore, the claimed invention as recited in the claims that follow is not limited to the embodiments described herein.

The invention claimed is:

1. A method for generating an intraoperative three-dimensional (3D) brain model while a patient is operated, the method comprising:
   before an opening in a patient's skull is made:
      providing a preoperative 3D brain model of a patient's brain;
      converting the preoperative 3D brain model to a preoperative 3D brain point cloud;
      providing a preoperative 3D face model of a patient's face; and
      converting the preoperative 3D face model to a preoperative 3D face point cloud;
   after the opening in the patient's skull is made:
      receiving an intraoperative 3D face point cloud and an intraoperative 3D brain point cloud;
      matching the intraoperative 3D face point cloud with the preoperative 3D face point cloud to find a face point transformation;
      transforming the intraoperative 3D brain point cloud based on said face point cloud transformation;
      comparing the intraoperative 3D brain point cloud with the preoperative 3D brain point cloud to determine a brain shift; and
      converting the preoperative 3D brain model to generate an intraoperative 3D brain model based on said brain shift.

2. The method according to claim 1, further comprising generating the preoperative 3D brain model based on preoperative magnetic resonance imaging scan of patient's brain.

3. The method according to claim 1, further comprising generating the preoperative 3D face model based on preoperative computed tomography scan of patient's face.

4. The method according to claim 1, further comprising receiving the intraoperative 3D face point cloud and the intraoperative 3D brain point cloud from a stereoscopic depth camera, a camera using projected light or a time of flight 3D sensor.

5. The method according to claim 1, further comprising determining the brain shift for the intraoperative 3D brain point cloud received as first after the opening in the patient's skull is made by using rigid transformation algorithms and for subsequent intraoperative 3D brain point clouds received, by using elastic registration algorithms.

6. A computer-implemented system, comprising:
   at least one nontransitory processor-readable storage medium that stores at least one of processor-executable instructions or data; and
   at least one processor communicably coupled to at least one nontransitory processor-readable storage medium, wherein at least one processor is configured to perform the steps of a method for generating an intraoperative 3D brain model while a patient is operated, the method comprising:
      before an opening in a patient's skull is made:
         providing a preoperative 3D brain model of a patient's brain;
         converting the preoperative 3D brain model to a preoperative 3D brain point cloud;
         providing a preoperative 3D face model of a patient's face; and
         converting the preoperative 3D face model to a preoperative 3D face point cloud;
      after the opening in the patient's skull is made:
         receiving an intraoperative 3D face point cloud and an intraoperative 3D brain point cloud;
         matching the intraoperative 3D face point cloud with the preoperative 3D face point cloud to find a face point transformation;
         transforming the intraoperative 3D brain point cloud based on said face point cloud transformation;
         comparing the intraoperative 3D brain point cloud with the preoperative 3D brain point cloud to determine a brain shift; and
         converting the preoperative 3D brain model to generate an intraoperative 3D brain model based on said brain shift.

7. The computer-implemented system according to claim 6, wherein the at least one processor is configured to perform the step of generating the preoperative 3D brain model based on preoperative magnetic resonance imaging scan of patient's brain.

8. The computer-implemented system according to claim 6, wherein the at least one processor is configured to perform the step of generating the preoperative 3D face model based on preoperative computed tomography (CT) scan of patient's face.

9. The computer-implemented system according to claim 6, wherein the at least one processor is configured to perform the step of receiving the intraoperative 3D face point cloud and the intraoperative 3D brain point cloud from a stereoscopic depth camera, a camera using projected light or a time of flight 3D sensor.

10. The computer-implemented system according to claim 6, wherein the at least one processor is configured to perform the step of determining the brain shift for the intraoperative 3D brain point cloud received as first after the opening in the patient's skull is made by using rigid transformation algorithms and for subsequent intraoperative 3D brain point clouds received, by using elastic registration algorithms.

* * * * *